United States Patent [19]

Fisher

[11] 4,095,454
[45] Jun. 20, 1978

[54] THERMAL INSULATION DEMONSTRATION DEVICE

[76] Inventor: Tom Fisher, 1695 E. Maple, Troy, Mich. 48084

[21] Appl. No.: 801,614

[22] Filed: May 31, 1977

[51] Int. Cl.² .................. G01N 25/18; G09B 23/16
[52] U.S. Cl. .................................. 73/15 A; 35/19 R; 35/50
[58] Field of Search .............. 73/15 A; 35/19 R, 10, 35/50; 219/367, 400

[56] References Cited

U.S. PATENT DOCUMENTS

| | | | |
|---|---|---|---|
| 2,296,815 | 9/1942 | Evans | 73/15 |
| 2,326,194 | 8/1943 | Barton | 73/15 |

*Primary Examiner*—Herbert Goldstein
*Attorney, Agent, or Firm*—Barnes, Kisselle, Raisch & Choate

[57] ABSTRACT

A device for demonstrating the relative effectiveness of various types of thermal insulation having a plenum chamber, at least two cells each communicating with the plenum chamber and receiving a quantity of insulation therein, and a separate after chamber communicating with each cell and the atmosphere with a thermometer received therein. A portion of a stream of heated air under pressure discharged into the plenum chamber passes through each cell and its associated after chamber and is discharged into the atmosphere. The differences in the temperature, as indicated by the thermometers, of the stream of air passing through each after chamber provide a visual indication of the relative effectiveness of the insulation in each cell and such differences in temperature can be physically sensed by a person who successively places a hand in the stream of air discharged to the atmosphere from each after chamber.

10 Claims, 5 Drawing Figures

THERMAL INSULATION DEMONSTRATION DEVICE

This invention relates to thermal insulation and more particularly to a device for testing and demonstrating the relative effectiveness of various types of thermal insulation.

Thermal insulation of various types of materials are commonly installed and used in both new and existing structures such as commercial buildings, apartments and houses. In existing structures thermal insulation is commonly installed by pouring or pneumatically blowing loose fibers of insulation between the studs of exterior walls and the joists of floors and ceilings. The same thickness of thermal insulation from various types of materials such as cellulose fibers, mineral rock wool, and fiberglass, have substantially different coefficients of thermal conductivity or insulating value. Thus, it is desirable to be able to quickly test and vividly demonstrate to building designers, construction material suppliers, lumberyards, homeowners, and other prospective purchasers and users of thermal insulation, the substantial differences in the relative effectiveness of the various types of insulation so that prospective purchasers and users can make an informed and intelligent selection of the type of thermal insulation to be installed in a structure.

A previous known device for demonstrating the relative effectiveness of various types of thermal insulation has an electric heat lamp suspended above and shining directly down on samples of various types of thermal insulation of the same thickness. In this device a thermometer is embedded in each sample of thermal insulation to provide a visual indication of the relative effectiveness of the various types of insulation. In operation of this device the heat lamp had to be turned on for about 25 to 45 minutes before the thermometers embedded in the insulation provided an indication of the relative effectiveness of the various types of insulation.

In the present invention a stream of heated and pressurized air passes from a plenum through each of at least two cells each containing a different type of thermal insulation and associated after chambers each containing a thermometer providing a visual indication of the relative effectiveness of the insulation in each cell and is discharged from each after chamber to the atmosphere. The relative effectiveness of the different types of thermal insulation can also be physically sensed by a person who places a hand in the stream of air discharged from each after chamber and thereby feels the difference in the temperature of the air flowing through each after chamber. The present invention under normal operating conditions demonstrates both visually and physically the relative effectiveness of different types of thermal insulation in less than two minutes after being energized.

Objects, features and advantages of this invention are to provide a device which quickly, effectively, and easily demonstrates both visually and physically the relative effectiveness of different types of thermal insulation, has a long service free life, and is rugged, durable, relatively inexpensive, and of economical manufacture and assembly.

These and other objects, features and advantages of this invention will be apparent from the following detailed description, appended claims, and accompanying drawings in which:

Figure 1:
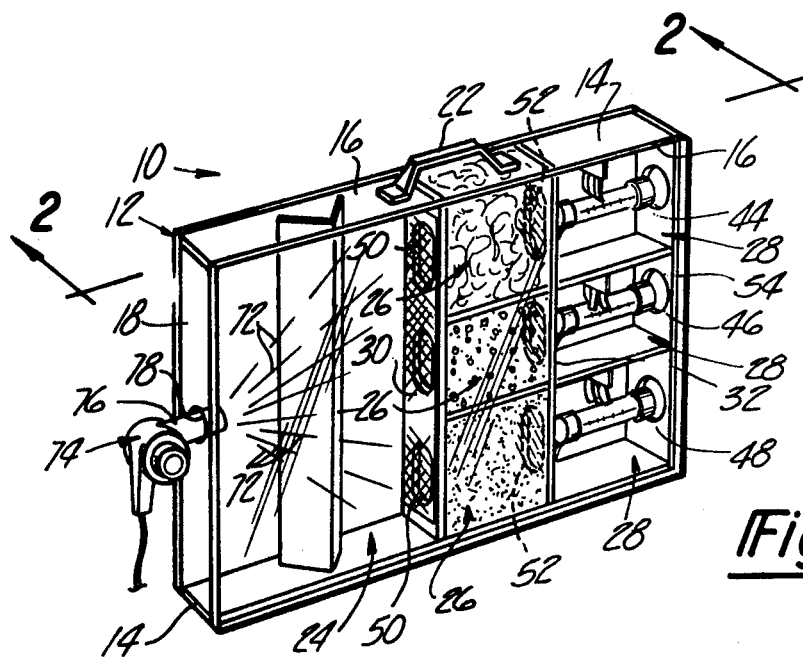
FIG. 1 is an isometric view of a thermal insulation demonstration device embodying this invention.
Figure 2:
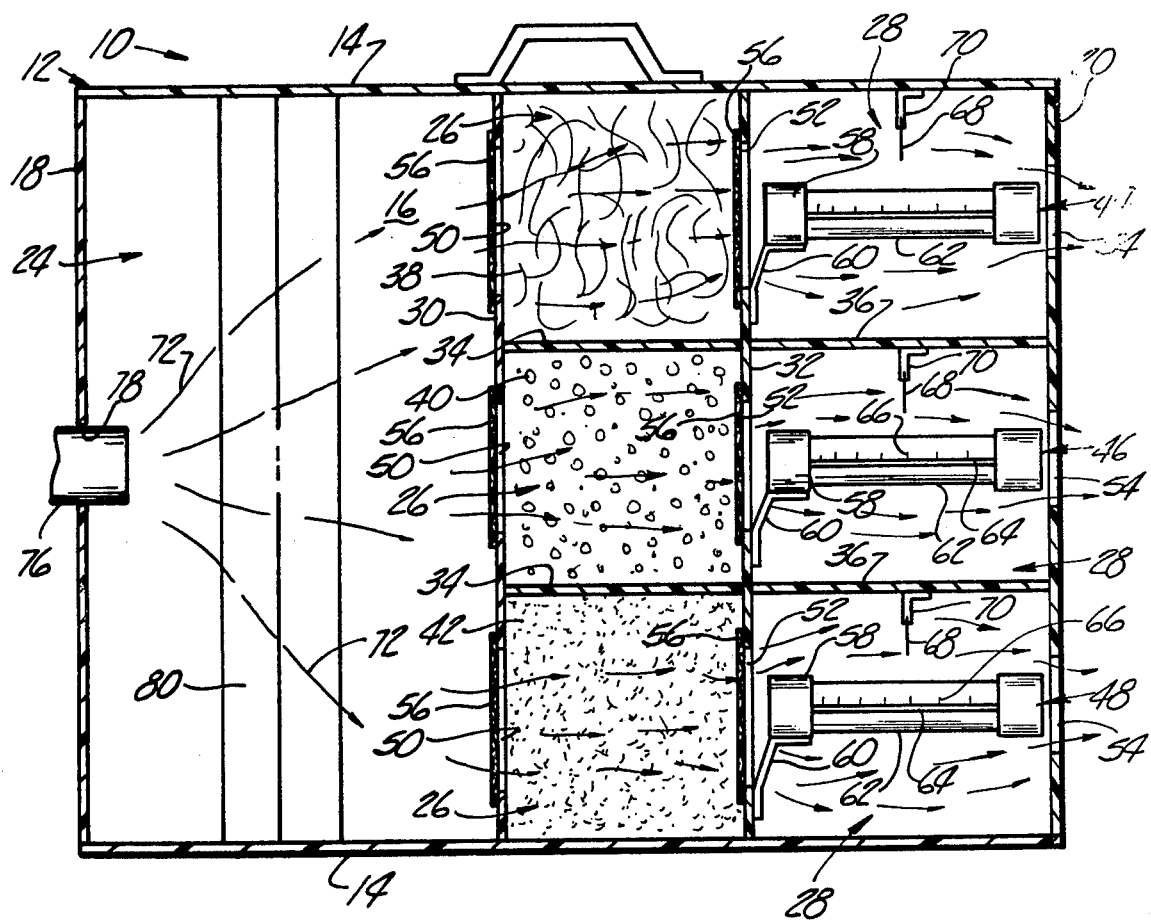
FIG. 2 is a sectional view on line 2—2 of FIG. 1.
Figure 3:
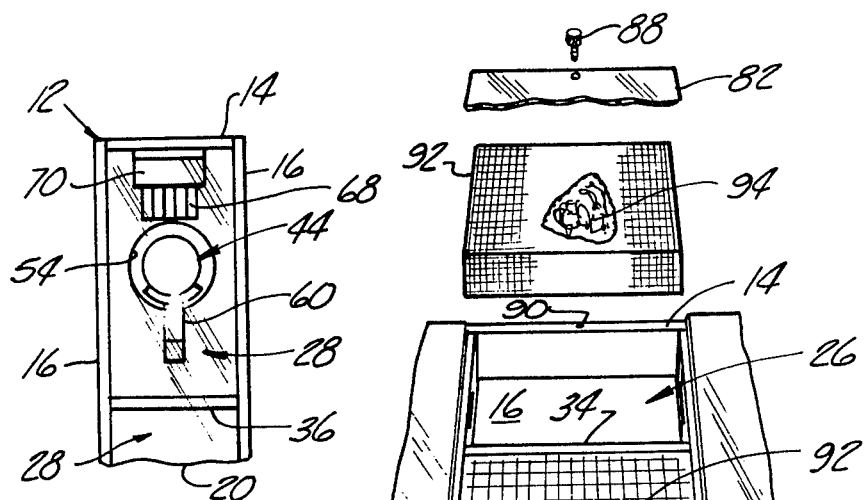
FIG. 3 is a fragmentary end view of the device of FIG. 1.

Referring in more detail to the drawings, FIGS. 1–3 illustrate a thermal insulation test and demonstration device 10 embodying this invention and having a generally rectangular and transparent case 12 with top and bottom walls 14, side walls 16, and end walls 18 and 20. A carrying handle 22 is fixed to top wall 14 and preferably case 12 is small enough to be portable and conveniently carried in one hand much like a large brief case. A substantially air tight plenum 24, three separate cells 26 for receiving insulation, and three separate after chambers 28 are formed in case 12 by two partitions 30 and 32, and divider walls 34 and 36. Each cell 26 is filled with a different type of insulation such as mineral rock wool 38, cellulose fiber 40, and fiberglass 42 insulation and each after chamber 28 has a separate thermometer 44, 46 and 48 therein.

Each cell 26 of insulation is of substantially the same size and volume and communicates with plenum 24 and only one after chamber 28 through elongate ports 50 and 52 in partitions 30 and 32. Each after chamber 28 communicates with the atmosphere through an outlet port 54 in end wall 20. The insulation in each cell 26 is prevented from escaping through ports 50 and 52 by a screen 56 overlying each port and secured to its associated partition 30 or 32. Thermometers 44, 46 and 48 are each removably mounted in an after chamber 28 by a retainer ring 58 secured to a bracket 60 fixed to partition 32. Each thermometer can be inserted into and removed from an after chamber 28 through outlet port 54 and has an outer tubular case 62 of glass one end of which may be inserted into and frictionally releasably retained in ring 58. Each thermometer indicates the temperature of the air within its associated chamber 28 and preferably is of conventional construction with a fine tube of glass 64 containing a liquid such as mercury or colored alcohol and a numbered scale 66. Optionally, a visual indication of the flow of a stream of air through each after chamber 28 is provided by streamers 68 carried by a bracket 70 mounted in the after chamber.

In device 10 a stream of heated air under pressure indicated by arrows 72 is supplied to plenum 24 by a blower unit 74 with an outlet duct 76 extending through an inlet port 78 in wall 18. The stream of heated air from blower 74 is at least partially diffused by an L shaped plate 80 within and extending across plenum 24 to provide a more uniform distribution of heated air to each cell 26. Blower unit 74 contains an electric heater element such as a nicrome wire and a fan driven by an electric motor which draws air from the atmosphere, passes the air over the electric heater element, and discharges through duct 76 a stream of hot air 72 under pressure. Preferably blower unit 74 is a conventional, lightweight, portable and normally hand held hair styler or dryer such as the hair styler commercially produced and sold under the trademark "Professional Stylist" by Grandinetti Products of Lynwood, Calif., which has a 1,000 watt heater element. Preferably there is a slight clearance between outlet duct 76 of blower unit 74 and inlet port 78 so that the blower unit can be removed and disconnected from case 12 when test and demonstration device 10 is not being used.

Figure 4:
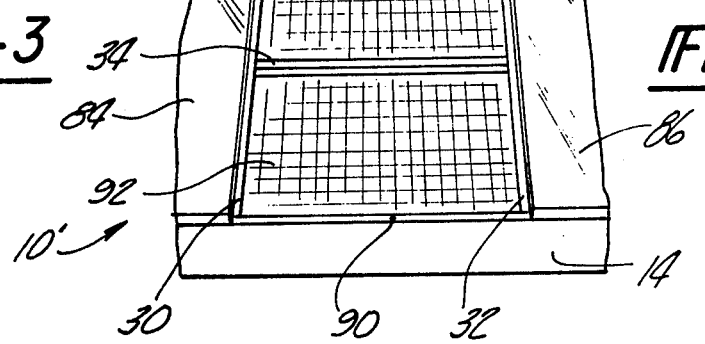
FIG. 4 is a fragmentary isometric view of a modified form of the device of FIG. 1 with cells in which samples of various types of insulation are removably inserted.

FIG. 4 illustrates a modified test and demonstration device 10' which is the same as device 10 except that cells 26 are arranged so that samples of various types of thermal insulation can be readily inserted into and removed from each cell. In device 10' one of the side walls is in three sections 82, 84 and 86 with end sections 84 and 86 fixed to the edges of walls 14, 18, 20 and of partitions 30, 32 of case 12, and center section 82 removably receivable between the end sections and securable on the edges of walls 14 by a pair of knurled screws 88 receivable in threaded holes 90 in walls 14. Generally rectangular baskets 92 of wire screen are removably receivable in each cell 26 and are each filled with an insulation 94. By providing a variety of baskets 92 each filled with either a different type of thermal insulation or thermal insulation produced by various manufacturers device 10' can be quickly and easily used to test and demonstrate the relative effectiveness of various types of thermal insulation produced by various manufacturers.

Figure 5:
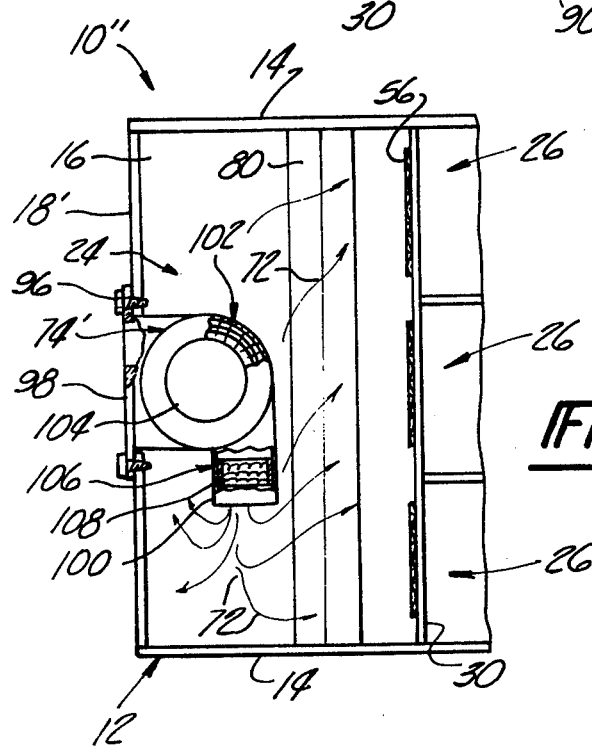
FIG. 5 is a fragmentary view partially in section of another modified form of the device of FIG. 1 with a blower and a heating element permanently mounted within the plenum.

FIG. 5 illustrates a modified testing and demonstration device 10" which is the same as device 10 except that a blower and heating unit 74' is permanently mounted by screws 96 in plenum 24 of case 12 for discharging a stream of heated air 72 under pressure into plenum 24. Unit 74' has an air inlet duct 98 communicating with the atmosphere, outlet duct 100 opening into plenum 24, and squirrel cage blower blades 102 driven by an electric motor 104. An electric heater 106 with a plurality of nicrome wire heating elements 108 is mounted in outlet duct 100 so that when electric motor 104 and heater 106 are energized air from the atmosphere is directed over heater elements 108 to produce a pressurized stream of heated air 72.

In the operation of devices 10, 10' and 10" heater and blower unit 74 or 74' is energized to discharge a stream 72 of heated and pressurized air into plenum 26 and over defuser 80. As indicated in FIG. 2 a portion of the stream 72 of heated air passes through each cell 26 and its associated after chamber 28 and is discharged to the atmosphere through a port 54. The temperature of the heated air passing though each after chamber is dependent on the coefficient of thermal conductivity of the insulation in its associated cell and hence the relative effectiveness of the various types of insulation is demonstrated by visually observing the difference in the temperature of the air stream in each after chamber 28 as indicated by thermometers 44, 46 and 48. The difference in the temperature of the air stream passing through each after chamber and hence the relative effectiveness of the various types of insulation in the associated cells can also be physically sensed by a person who successively places his fingers in front of the outlet port 54 of each after chamber 28. After the blower and heater unit 74 or 74' has operated for a few minutes the temperature of the stream of air passing through each after chamber 28 will usually become stable. When the samples of insulation are rock wool, cellulose fiber, and fiberglass there will be substantial differences between the temperatures of the streams of air flowing through each of the after chambers thereby quickly, dramatically and vividly demonstrating substantial differences in the relative effectiveness of the same thickness of each of these three types of thermal insulation.

Preferably all of the partitions, dividers, diffuser plates, and walls of cases 12 of all forms of this test and demonstration device are made of panels of sheets of a transparent, clear, tough and durable material such as sheets of acrylic plastic sold under the trademark Plexiglas. The various partitions, dividers, plates and walls can be secured together in assembled relation by a suitable adhesive or glue such as Almac Acrylic Adhesive H-94, sold by Almac Acrylics, 26400 Groseback Highway, Warren, Mich.

Plastic sheets of one-quarter inch thick Plexiglas have proved satisfactory to construct a device in substantially the form shown in FIG. 1-3 with a rectangular case having exterior dimensions of three inches in depth, eighteen inches in width, and twenty-four inches in length with each cell having substantially the same interior volume and an interior length of 6 inches and each after chamber having substantially the same interior volume and an interior length of 8 inches. In this device the three insulation cells were completely filled with mineral wool, cellulose fiber, and fiberglass insulation as shown in FIGS. 1 and 2. When the aforementioned Grandinetti Prodcuts hair dryer is used as a blower unit 74 for this device and operated in atmospheric air at a room temperature of about 70° Fahrenheit, after about one minute of continuous operation of the blower and the heater unit 74 set on its high heat position, the thermometers 44, 46 and 48 indicate the temperature of the air stream flowing through their associated after chambers of about 97° F., 74° F. and 110° F. respectively. After about eight minutes of continuous operation of blower unit 74 while set on its high heat position, the temperature of the air stream flowing through each of the after chambers 28 becomes substantially stabilized at the temperatures indicated by thermometers 44, 46 and 48 of about 150° F., 91° F. and 156° F. respectively. The differing temperatures recorded by thermometers 44, 46 and 48 indicate the relative efficiency of the various types of thermal insulation and if desired these differences in relative efficiency can also be physically sensed by a person successively positioning his fingers in front of the outlet port 54 of each after chamber 28.

By making the walls, partitions, dividers, and diffuser of the case 12 of devices embodying this invention from a clear and transparent material, the contruction and arrangement of the entire test and demonstration device is readily apparent to and can be quickly comprehended by an observer of the device which is particularly reassuring to any person who is skeptical of or perhaps disinclined to believe the substantial differences demonstrated by this device in the effectiveness of the same thickness of different types of thermal insulation. Likewise the removable mounting of the thermometers permits any person who is skeptical of their accuracy to switch the thermometers around to different after chambers to prove that they are accurate and functioning properly. Moreover, the removable mounting also permits any inaccurate or damaged thermometers to be quickly removed and replaced with accurate and properly functioning thermometers.

I claim:

1. A thermal insulation demonstration device comprising at least two insulation cells each constructed and arranged to receive a quantity of thermal insulation therein, a plenum communicating with said insulation cells and constructed and arranged to direct heated air under pressure into each of said insulation cells, a separate after chamber for each of said insulation cells, each after chamber having an inlet communicating with its associated insulation cell downstream of the communication of such insulation chamber with said plenum and constructed and arranged to receive heated air from its associated insulation chamber, a thermometer received in each after chamber, and each after chamber having a transparent portion constructed and arranged so that its associated thermometer can be visually observed and read from the exterior of the device, whereby when different types of thermal insulation are received in the insulation cells and heated air passes from said plenum through said insulation cells and into said after chambers the relative effectiveness of the different types of thermal insulation is demonstrated by the temperatures in the after chambers measured by the thermometers.

2. The device of claim 1 wherein each after chamber also has an outlet spaced from said inlet and mounting means removably mounting each of said thermometers in its associated after chamber and constructed and arranged so that such thermometer can be inserted into and removed from its associated after chamber through its associated outlet.

3. The device of claim 1 wherein each after chamber also has an outlet spaced from and downstream of said inlet and constructed and arranged to permit a person to place his fingers successively in front of each outlet for sensing the temperature of a stream of air discharged therefrom after it has passed from said plenum chamber through one of said cells and its associated after chamber.

4. The device of claim 1 wherein said plenum has an inlet constructed and arranged for releasable connection with the outlet duct of a normally hand held portable hair dryer having an electric heater element and a blower and constructed and arranged to discharge a stream of heated air through said outlet duct.

5. The device of claim 4 wherein each after chamber also has an outlet spaced from said inlet and mounting means removably mounting each of said thermometers in its associated after chamber and constructed and arranged so that such thermometer can be inserted into and removed from its associated after chamber through its associated outlet.

6. The device of claim 1 wherein at least a portion of each of said insulation cells is transparent and permits visual observation from the exterior of th device of insulation received in each insulation cell.

7. The device of claim 5 wherein at least a portion of said plenum is transparent and permits visual observation from the exterior of the device of the interior of said plenum.

8. The device of claim 1 which also comprises a blower having an outlet connected to said plenum, an electric motor drivably coupled to said blower, and an electric heater element associated with said blower and plenum to heat air supplied by said blower to said plenum.

9. The device of claim 1 wherein each of said after chambers has an outlet and which also comprises a streamer mounted in each of said after chambers between the inlet and outlet thereof, and positioned so as to be visually observable from the exterior of the device.

10. The device of claim 1 which also comprises a perforate container with thermal insulation therein and constructed and arranged to be removably received in one of said insulation cells.

* * * * *